United States Patent [19]
Qin et al.

[11] Patent Number: 5,633,259
[45] Date of Patent: May 27, 1997

[54] METHOD FOR IDENTIFICATION OF LOW/NON-ADDICTIVE OPIOID ANALGESICS AND THE USE OF SAID ANALGESICS FOR TREATMENT OF OPIOID ADDICTION

[75] Inventors: Bo-yi Qin; Xiong-qi Gong; Mao Huang; Li-Jun Sha, all of Beijing, China; Chang Yi Wang, Cold Spring Harbor, N.Y.

[73] Assignee: United Biomedical, Inc., Hauppauge, N.Y.

[21] Appl. No.: 387,679

[22] Filed: Feb. 13, 1995

Related U.S. Application Data

[63] Continuation of Ser. No. 88,503, Jul. 7, 1993, abandoned, which is a continuation-in-part of Ser. No. 977,332, Nov. 17, 1992, abandoned, which is a continuation-in-part of Ser. No. 947,690, Sep. 21, 1992, abandoned.

[51] Int. Cl.$^6$ .................. A61K 31/44; A61K 31/135
[52] U.S. Cl. .................. 514/282; 514/648; 514/812
[58] Field of Search .................. 514/282, 648, 514/812

[56] References Cited

U.S. PATENT DOCUMENTS

| | | | |
|---|---|---|---|
| 3,879,555 | 4/1975 | Pachter et al. | 514/648 |
| 3,885,027 | 5/1975 | Shaw et al. | 514/812 |

FOREIGN PATENT DOCUMENTS 2188843  10/1987  United Kingdom.

OTHER PUBLICATIONS

CA117:666F Wang et al., (Zhongguo Yaolixw Yu DulixueZazhi, 1992, 6(1), 36–40).

CA72:119700, VonCube et al., /Naunyn–Schmiedebergs Arch. Pharmakol., 265(5) 455–73 1970).

The Mack Trdux, 11th ed., Merck & Co., Inc., NJ, 1989, pp. 610–611 & 936.

Huang and Qin, *Acta Pharmacologica Sinica* 3: 9–13 (1982) Analgesic and Other CNS Depressive Effects of Dihydroetorphine.

Huang and Qin, *Acta Pharmacologica Sinica* 3: 81–84 (1982) Physical Dependence of Dihydroetorphine in Mice and Monkeys.

Cao et al, Chin. J. Clin. Pharmacol. 6: 54–59 (1990) Drug Dependence on Dihydroetorphine.

Wang, Liu and Qin, *Chinese J. Pharmacology and Toxicology* 6: 36–40 (1992) Experimental therapeutic effects of dihydroetorphine in morphine–dependent rats and monkeys.

Huang et al, Acta Pharmacologica Sinica 9: 308–312 (1988) Pharmacodynamics and Pharmacokinetics of Dihydroetorphine Hydrochloride administered Sublingually in Mice and Rats.

Wu and Sun, Chung Hua Chung Liu Tsa Chih 13: 64–67 (1991) Dihydroetorphine Hydrochloride for Moderate and Severe Cancer Pain.

Thorn–Gray and Levitt, *Behavioral Neuroscience*, 97(5) 768–778 (1983) Rat Brain sites responsive to etorphine: Analgesia and catatonia.

Williams et al, Proc. Soc. Exp. Biol. Med., 131 (1) 97–100 (1969). Analgesic tolerance to etorphine and morphine in the mouse.

(List continued on next page.)

*Primary Examiner*—José G. Dees
*Assistant Examiner*—Mary C. Cebucak
*Attorney, Agent, or Firm*—Morgan & Finnegan, L.L.P.

[57] ABSTRACT

The present invention relates to a method of using a bioassay consisting of an electrophysiological method and a cell culture system of dorsal-root ganglion (DRG) neurons to screen and identify opioids with a high potential for use as "low- or non-addictive" analgesics. Another aspect of the invention relates to a specific group of opioid alkaloids and analogues thereof identified by the bioassay of the invention for the unique ability to activate only inhibitory, but not excitatory, opioid receptor function, for use as low- or non-addictive analgesics. Another aspect of the invention relates to the specific use of etorphine or dihydroetorphine of the opioid alkaloid family as low- or non-addictive analgesics and for the treatment of opioid addiction.

6 Claims, 7 Drawing Sheets

OTHER PUBLICATIONS

Blane, J. Pharm. Pharmac. 19, 781–782 (1967) Absence of respiratory depression in the newborn rat after maternal administration of etorphine by sublingual route.

Shen and Crain, Brain Research, 531, 1–7 (1990) Cholera toxin–B subunit blocks excitatory effects of opioids on sensory neuron potentials indicating that GM1 ganglioside may regulate Gs–linked opioid receptor functions.

Crain and Shen, Trends in Pharmacological Sciences, 11(2), 1–7 (1990) Opioids can evoke direct receptor–mediated excitatory effects on sensory neurons.

Bentley et al, Nature, 206, 102–103 (1965) Compounds possessing Morphine–antagonizing or Powerful Analgesic Properties.

Bently and Hardy, Proc. Chem. Soc., p. 220 (1963) New potent analgesics in the morphine series.

Bently and Hardy, J. Am. Chem. Soc. 89, 3281–3286 (1967) Novel analgesics and molecular rearrangements in the morphine–thebaine group III. Alcohols of the . . . .

Blane and Robbie, Brit. J. Pharma. Chemother. 20, 252–253 (1970) Trial of etorphine hydrochloride (M99 Reckitt) in carcinoma pain: A preliminary report.

Blane et al., Brit. J. Pharma. Chemother. 30, 11–22 (1967) Action of etorphine hydrochloride (M99): A Potent Morphine–like agent.

Jasinski et al, Clin. Pharma. Ther. 17, 267–272 (1975) Etorphine in Man I. Subjective effects and supression of morphine abstinence.

WHO Expert Committee on Dependence–producing Drugs, Fifteenth Report, p. 5 (1966).

Attali et al, Brain Research, 517, 182–188 (1990) Characterization of kappa opiate receptors in rat spinal cord–DRG cultures and their regulation by chronic.

Cho et al, Proc. Nat'l. Acad. Sci. 80, 5176–5180 (1983) Isolation of opiate binding components by affinity chromatography and reconstruction of binding active.

MacDonald et al, Science, 199, 1449–1451 (1978) Specific opiate induced depression of transmitter release from DRG cells in culture.

Qin and Huang, International Symposium on New Drug Research and Development Beijing, China, (Oct. 1991), Research Advance and Clinical Application of Highly Potent Dihydroetorphine Hydrochloride.

Qin, 5th National Congress of Neuropharmacology, Mar. 1992 Progress in Research of Dihydroetorphine: From an Analgesic to Substitution Agent in Treatment of Drug Addiction.

Kosterlitz and Waterfield, Ann. Rev. Pharmacol. 15, 29–47 (1975) InVitro Models in the Study of Structure–Activity Relationships of Narcotic Analgesics.

Qin, New Drugs and Clinical Remedies, 1992 Research Advances of Dihydroetorphine: From Analgesia to Detoxification.

Wang et al, Chin. J. Clin. Pharmacol. 1992; 8(2): 106–112 Clinical Investigation on Detoxification of Heroin Addiction with Dihydroetorphine Hydrochloride.

1. BSS
2. Etorp 1fM
3. Etorp 1pM

4. Etorp 1nM
5. Etorp 1uM
6. BSS 20 mV
10 ms

1. DADLE 1uM
2. DADLE + Dyn 1fM
3. DADLE + Dyn 1nM
4. DADLE + Dyn 1μM

5. DADLE 1uM
6. DADLE + Etorp 1fM
7. DADLE + Etorp 1pM
8. DADLE + Etorp 1nM
9. DADLE + Etorp 1μM
10. DADLE 1uM 20 mV
10 ms 1. DADLE 1uM
2. DADLE + NLX 1nM
3. DADLE + NLX + Etorp 1pM
4. DADLE + NLX + Etorp 1nM

METHOD FOR IDENTIFICATION OF LOW/ NON-ADDICTIVE OPIOID ANALGESICS AND THE USE OF SAID ANALGESICS FOR TREATMENT OF OPIOID ADDICTION

CROSS REFERENCE TO RELATED APPLICATIONS

This is a continuation application of application Ser. No. 08/088,503 filed Jul. 7, 1993, now abandoned, which is a continuation-in-part application of application Ser. No. 977,332 filed Nov. 17, 1992, now abandoned, which is a continuation-in-part application of Ser. No. 947,690 filed Sep. 21, 1992, abandoned.

This invention was made in part with Chinese Government support under research grants CO3020801 awarded by National Foundation of Sciences of China, 85-922-02-22 awarded by Foundation of National Committee of Science and Technology of China; and 9009120 awarded by AMMS Research Grant; and support from United Biomedical Inc.'s general research fund.

FIELD OF THE INVENTION

The present invention relates to a specific group of opioid agonists for use as low/non-addictive analgesics and for treatment of opioid addiction. More particularly, the present invention is directed to etorphine, dihydroetorphine, and other opioid and analogues thereof that are effective as low/non-addictive analgesics and for the treatment of opioid addiction. In addition, this invention provides a bioassay method to screen and identify such compounds with the ability to selectively activate inhibitory but not excitatory opioid receptor-mediated functions.

BACKGROUND OF THE INVENTION

Since the introduction of morphine to the clinic as a pain reliever, clinicians have been troubled with the problem of drug addiction. For more than a century, chemists, pharmacologists, and clinicians have strived to find an ideal analgesic with high potency, yet low addictivity. A series of opioids such as meperidine, methadone, and fentanyl were subsequently developed.

However, none of these drugs exert sustained analgesic effects in patients without developing addiction. In Western countries, methadone substitution has been employed for the treatment of drug abuse for some time. Unfortunately, methadone induces significant psychological and physical dependencies. Consequently, patients undergoing such treatment usually convert to methadone dependence during withdrawal from chronic use of morphine, heroin or other opioids (Jaffe, 1990). Therefore the need remains to develop better methods based upon insights into the molecular and cellular mechanisms underlying opioid addiction for treating drug abuse and particularly a means to identify compounds for use as low- or non-addictive analgesics and for suppression of opioid withdrawal symptoms.

SUMMARY OF THE INVENTION

The present invention is directed to an in vitro screening method for identifying a low- or non-addictive opioid analgesic by screening opioids to identify a compound which is capable of evoking an inhibitory effect but not an excitatory effect on opioid receptor-mediated functions of sensory neurons in a dose-dependent manner over the concentration range of from about femtomolar (fM) to about micromolar (μM). In particular, such opioid compounds are identified by recording the action potential duration (APD) of a sensory neuron elicited by the compound in a cell culture screening assay and selecting those opioid compounds which shorten the APD but do not prolong the APD relative to a control APD when the compounds are assayed in the concentration range of about fM to about μM. Opioid compounds with these characteristics are thereby identified as low- or non-addictive opioid analgesics of the invention. Preferably, the cell culture screening assay comprises exposing a dorsal-root ganglion (DRG) neuron to the candidate compound, typically by bath perfusion, applying a brief intracellular depolarizing current to said DRG neuron, and recording opioid-induced alteration in the APD of the DRG neuron using standard electrophysiological techniques.

Another aspect of the invention, thus, provides low- or non-addictive analgesics, particularly as identified by the method of the present invention, which are capable of evoking the inhibitory but not the excitatory effects of opioid receptor-mediated functions, particularly on sensory neutrons, in a dose-dependent manner in concentrations ranging from about fM to about μM. In a preferred embodiment these opioids include etorphine or dihydroetorphine. Pharmaceutical compositions containing the subject low- or non-addictive opioids, or pharmaceutically acceptable salts thereof, together with pharmaceutically acceptable carriers are also provided.

Yet another aspect of this invention provides a method of treating opioid addiction by administering an effective amount of a non-addictive opioid analgesic, or an analog thereof, to a patient for a time sufficient to relieve or suppress withdrawal symptoms that occur when the addictive opioid is withheld from the addict. After the initial administration of the non-addictive opioid analgesic for a period to permit alleviation of the withdrawal symptoms, the dose of the non-addictive opioid analgesic is gradually decreased from the original dose to zero over time sufficient to fully wean said patient from said analgesic without untoward side effects. Typically the initial administration of the non-addictive opioid analgesic lasts for about 1 to about 5 days and the weaning period lasts from about 1 to about 7 days, so that a patient can be withdrawn from opioid addiction within an overall about 2 to 12 day period. In a preferred embodiment the non-addictive opioid analgesic is etorphine or dihydroetorphine initially administered at a dose of from about 10 μg to about 1000 μg per day. Such dosages are usually administered sublingually, intramuscularly or intravenously, preferably by intravenous dripping, depending on the severity of the withdrawal symptoms in the patient. Even more preferably, opioid addiction is treated by administering about 40 to about 500 μg of dihydroetorphine per day to a patient for about one to about three days, administering a decreasing amount of dihydroetorphine for the following about four to about seven days so that no further dihydroetorphine is necessary by about 10 days after the first administration of dihydroetorphine.

A further aspect of the invention provides a method of treating opioid addiction by administering an effective amount of a non-addictive opioid analgesic, to a patient for a time sufficient for immediate relief or suppression of withdrawal symptoms due to said opioid addiction; administering an effective amount of a longer-acting replacement opioid for a time sufficient to maintain the relief or suppression of withdrawal symptoms, followed by administering a decreasing dose of the non-addictive opioid analgesic for a time sufficient to wean said patient from said opioid analgesic without untoward side effects. Typically the initial administration of the non-addictive opioid analgesic lasts for about 1 to about 3 days, the administration of the replacement opioid lasts for about 1 to about 3 days, and the return to the non-addictive opioid analgesic with its concomitant weaning period lasts from about 1 to about 8 days, so that a patient can be withdrawn from opioid addiction within an overall 3 to 14 day period.

In a preferred embodiment the non-addictive opioid analgesic is etorphine or dihydroetorphine initially administered at a dose of from about 10 μg to about 1000 μg per day. Such dosages are usually administered sublingually, intramuscularly or by intravenous dripping depending on the severity of the withdrawal symptoms in the patient. Preferably the replacement opioid is methadone administered per os at a dose of about 5–100 mg/day.

A still further aspect of the invention provides a method of treating acute or chronic pain with a low- or non-addictive opioid analgesic. In particular, dihydroetorphine hydrochloride (DHE) is administered to a patient for a time and in an amount effective to relieve or suppress pain without resultant addiction. Treatment for acute pain is typically accomplished by administration of about 20–60 μg DHE sublingually, up to about 180 μg per day for the duration of the pain, and typically no longer than 1 week. Treatment for chronic pain is typically accomplished by administration of about 20–100 μg DHE sublingually, up to 400 μg per day, and such administration can last several months. In rare instances treatment of chronic pain can result in mild addiction.

BRIEF DESCRIPTION OF ABBREVIATIONS USED

Figure 1A:
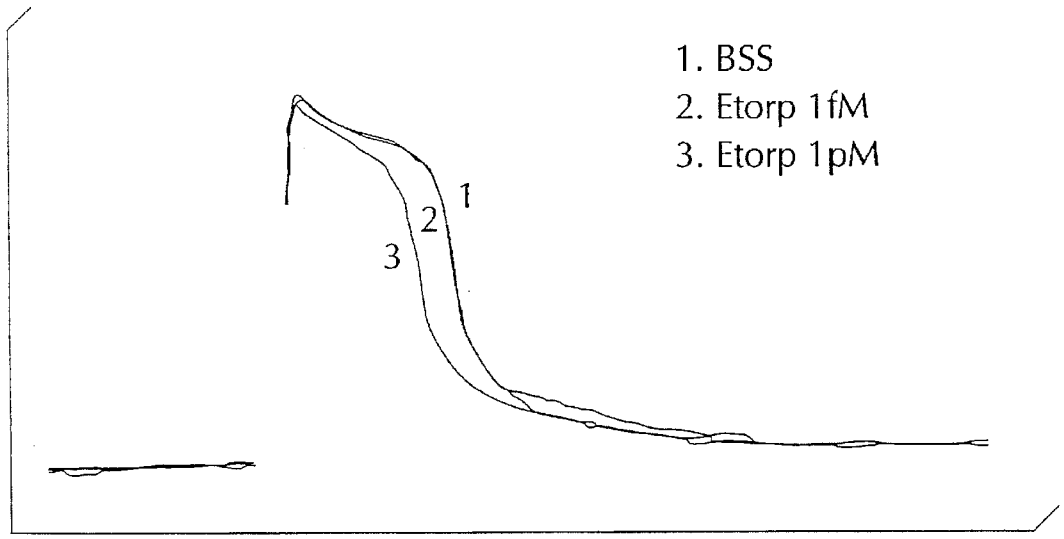
FIG. 1 illustrates that acute application of pM-μM concentrations of etorphine to a naive DRG neuron elicits inhibitory shortening of the APD. 1: Action potential (AP) generated by a DRG neuron in Hank's balanced salt solution containing 5 mM $Ca^{2+}$ and 5 mM $Ba^{2+}$ (BSS). AP response in this record (and in all records below) was evoked by a brief (2 msec) intracellular depolarizing current pulse. 2–5: The APD is progressively shortened by bath perfusion of 1 fM, 1 pM, 1 nM and 1 μM etorphine, respectively. 6: After washout of etorphine, the APD recovers.

| BRIEF DESCRIPTION OF ABBREVIATIONS USED | |
| --- | --- |
| DADLE | [D—Ala$^2$,D—Leu$^5$]enkephalin |
| DAGO | [D—Ala$^2$,MePhe$^4$, Gly-ol]enkephalin |
| DPDPE | Tyr—D—Pen—Gly—Phe—D—Pen (Pen = penicillamine) |
| U-50,488H | 3,4 dichloro-N-methyl-N-(2-[1-pyrrolidinyl]-cyclohexyl)benzene-acetamide |
| Dynorphin 1-13 | dynorphin A, Fragment 1-13 (Tyr—Gly—Gly—Phe—Leu—Arg—Arg—Ile—Arg—Pro—Lys—Leu—Lys) |
| Dynorphin 1-17 | dynorphin A, Fragment 1-17 (Tyr—Gly—Gly—Phe—Leu—Arg—Arg—Ile—Arg—Pro—Lys—Leu—Lys—Trp—Asp—Asn—Gln) |
| Etor | etorphine |
| DHE | dihydroetorphine |

DETAILED DESCRIPTION OF THE INVENTION

In accordance with the present invention, electrophysiologic assay of the effects of opioids on the action potential duration of sensory neurons in organotypic cultures provides an extremely sensitive in vitro bioassay to screen and characterize agonists with the ability to activate inhibitory, but not excitatory, opioid receptor-mediated functions. This assay permits identification of low- or non-addictive opioid analgesics as well as agents useful for treatment of drug addiction.

As used herein "non-addictive" and "low-addictive" are used interchangeably to describe the addiction potential of the opioids of the present invention. Ill treating opioid addiction in accordance with the present invention, the subject opioids are essentially non-addictive at the prescribed dosages when used for periods of up to several weeks. For example, DHE administration to a drug addict in the range of about 10 µg to about 1000 µg per day which is gradually withdrawn over a period of up to 14 days, does not result in addiction to DHE. In contrast, even well-controlled treatment of drug addicts by methadone substitution invariably results in transfer to methadone addiction. The present invention, thus, greatly improves the present methods for treating opiate drug abuse without concomitant addiction to another opioid.

Likewise, treatment of acute pain for several days with the subject opioids in accordance with the present invention, does not result in addiction. While treatment of chronic pain of long duration with the subject opioids generally does not result in addiction, mild addiction may result in exceptional cases. Hence use of the subject opioids in accordance with this invention is non-addictive for the vast majority of chronic pain patients. The addiction potential of the subject opioids, as illustrated with DHE, for chronic pain patients is thus low, ion, typically less than 1 in 100 for patients treated greater than 3 months. For example, no addiction has been observed in treating patients for up to 3 months with DHE. Moreover, in the rare cases of addiction, such addiction may have resulted from minor contaminants present in bimodally-acting thebaine, a starting material for drug synthesis, which is carried into certain preparations of DHE.

As used herein "opioid" refers to any substance that binds specifically to an opiate receptor (Casy & Parfitt, 1986; Pasternak 1988).

As used herein "replacement opioid" is a bimodally-acting opioid that has both inhibitory and excitatory effects on opioid receptors. Such opioids, generally, have a longer duration of action than the non-addictive opioid analgesics.

Activation of opioid receptors has been known to produce inhibitory effects on neuronal activity which in turn provides the primary cellular mechanism underlying opioid analgesia in vivo (e.g. North, 1986). However:, recent electrophysiological studies indicated that specific mu-, delta- and kappa-opioid receptor agonists elicit both excitatory and inhibitory modulation of the action potentials of sensory DRG neurons isolated ill culture in a concentration dependent manner (Shen & Crain, 1989; Crain & Shen, 1990).

These opioid agonists were found to elicit excitatory effects at low (<nM) concentrations and inhibitory effects at high (µM) concentrations as measured by prolongation or shortening of the calcium-dependent component of the action potential duration (APD), respectively (See U.S. Ser. No. 977,332 at FIG. 2 and herein at Table 1).

Earlier experiments demonstrated that the excitatory effects of opioids are mediated by opioid receptors that are positively coupled via a cholera toxin-sensitive Gs-like regulatory protein to adenyl cyclase and cyclic AMP-dependent voltage-sensitive ionic conductances (resembling, for example, beta-adrenergic receptors) (See U.S. Ser. No. 977,332 at FIG. 2; Shen & Crain, 1989, 1990a; Crain & Shen, 1990, 1992), whereas inhibitory effects are mediated by opioid receptors linked to pertussis toxin-sensitive Gi/Go proteins (resembling alpha$_2$-adrenergic receptors) (See U.S. Ser. No. 977,332 at FIG. 2; Shen & Crain, 1989; Gross et al, 1990).

The ability to differentiate between these bimodal properties of opioids, i.e. excitatory and inhibitory activities mediated by two distinct groups of opioid receptors, has led to the present invention, and particularly to a method for identifying low- or non-addictive opioid analgesics. Hence, this method provides an in vitro bioassay to identify compounds that can selectively activate the inhibitory but not excitatory opioid response. Since sustained activation of excitatory opioid receptor functions plays a crucial role in development of tolerance and dependence in chronic opioid-treated neurons in vitro (Crain & Shen, 1992; Shen & Crain, 1992), compounds with such properties, i.e. which activate the inhibitory response but not the excitatory response, are useful as non-addictive analgesics in vivo.

In particular, the in vitro bioassay uses a cell culture system of DRG neurons to screen candidate compounds by exposing the DRG neurons to the candidate compound and observing its effect on the APD using standard electrophysiological recording methods. The detailed methodology for growing neurons, treating with a candidate compound and recording the APD are provided in Example 1. Any opioid compound screened by this bioassay that exhibits inhibitory effects (e.g., shortening the APD in DRG neurons) but not excitatory effects (e.g., prolonging the APD in DRG neurons) in about the fM-pM range to µM range is a low- or non-addictive opioid analgesic in vivo. Generally, these compounds effect the APD in a concentration-dependent manner and the responses are mediated by specific opioid receptors. Hence, the method of the present invention provides a powerful tool to identify low- or non-addictive opioid analgesics.

Nearly all the opioids tested by this bioassay, including morphine, enkephalins, dynorphins, endorphins and synthetic opioid peptides, have dose-related dual modulatory effects (i.e. both inhibitory and excitatory effects) on the action potential of sensory DRG neurons. All such compounds are well-known to be addictive. However, in accordance with this invention etorphine and dihydroetorphine (thebaine derivatives) (Bentley and Hardy, 1963; Bentley and Hardy, 1967), compounds previously believed and classified as addictive (WHO Rep 1966), have the selective characteristic (Table 1) of inhibiting opioid-receptor mediated functions without exciting such functions. Both etorphine and dihydroetorphine elicit dose-dependent (inhibitory) shortening of the APD, starting at about pM levels in some of the DRG neurons, and reaching a maximum effect at μM levels in most of the DRG neurons (Example 1). Furthermore, no excitatory prolongation of the APD occurs with these two compounds at <pM concentrations in contrast to the characteristic excitatory effects elicited at low concentration by the bimodally-acting opioids.

It is well known that chronic exposure of DRG-spinal cord explants to bimodally-acting opioids (e.g., morphine or DADLE) causes sensory DRG neurons to become desensitized to the inhibitory effects of opioid agonists, resulting in tolerance (Crain et al, 1988), and supersensitized to the excitatory effects of opioid agonists as well as antagonists, resembling significant features of abstinence, dependence and withdrawal syndrome in vivo (Crain & Shen, 1992a,b; Shen & Crain, 1992).

Sustained activation of excitatory opioid receptors after chronic treatment with an opioid agonist triggers a positive-feedback mechanism that results in up-regulation of a Gs/adenylate cyclase/cyclic AMP/protein kinase A/GM1 glycosyl-transferase system that may account for the remarkable supersensitivity of chronically opioid-treated neurons to the excitatory effects of opioid antagonists and agonists (Crain & Shen, 1992a,b; Shen & Crain, 1992).

When DRG-cord explants are chronically treated with a bimodally-acting delta/mu agonist, DADLE (1 μM) or morphine (1 μg/ml) for 3 weeks, acute treatment with etorphine still elicits a marked inhibitory dose-dependent shortening of the APD of DRG neurons even at concentrations as low as 1 fM (Example 2), whereas bimodally-acting mu, delta and kappa opioid agonists show a high degree of opioid excitatory supersensitivity at concentrations ranging from pM to μM (Example 2).

Furthermore, the excitatory APD prolongation of chronic opioid-treated DRG neurons precipitated by acute application of nM naloxone (Crain & Shen, 1992a,b), which provides a cellular model of naloxone-induced withdrawal supersensitivity in opiate addicts in vivo (Crain & Shen, 1992b), can be blocked by acute application of etorphine, but not by morphine or other bimodally acting opioid agonists (Example 2).

Tissue culture studies provide strong support that excitatory opioid receptor functions of sensory neurons play important roles in vivo, both by attenuating analgesic effects mediated by inhibitory opioid receptors and by facilitating the cellular mechanisms underlying addiction. The use of opioids (e.g. etorphine, dihydroetorphine), that at low concentrations preferentially activate inhibitory but not excitatory opioid receptor functions in vitro, as indicated by the screening model, results in much more potent analgesia in vivo and far less evidence of dependence/addiction than occurs during chronic treatment with morphine and most other bimodally-acting opioids.

The present invention demonstrates that etorphine and compounds with similar properties as identified by the present bioassay (e.g. dihydroetorphine) elicit potent dose-dependent inhibitory APD-shortening effects on naive and chronic opioid-treated, "addicted" sensory DRG neurons, even at low (pM-nM) concentrations where most bimodally-acting opioids generally elicit excitatory APD-prolonging effects. Hence etorphine and similar compounds of this invention selectively activate inhibitory rather than excitatory opioid receptors on DRG neurons, even when the cells are supersensitive to the excitatory effects of bimodally-acting opioids following chronic treatment.

Etorphine has long been known to be >1,000 times more potent than morphine as an analgesic in animals (Blane et al, 1967) and humans (Blane & Robbie, 1970; Jasinski et al, 1975). This invention shows that the high inhibitory potency of etorphine may be due, in part, to its selective activation of inhibitory opioid receptors whose effects are not attenuated by the concomitant activation of higher-affinity excitatory opioid receptors.

The clinical trial results of the present invention show that low doses of dihydroetorphine, a specifically inhibitory opioid-receptor agonist, are remarkably effective in relieving postoperative pain and chronic pain in terminal cancer patients, yet tolerance and addiction are far less evident than observed with morphine and other conventional bimodally-acting opioids (Example 5). Thousands of patients have been treated with a 90% effective rate and no significant adverse side-effects have been observed.

In addition, several hundred heroin addicts have been successfully treated over a two year period. In this group, withdrawal symptoms were rapidly blocked and dihydroetorphine substitution therapy was maintained for about a week with minimal rebound after final opioid withdrawal (Example 6). Similar results were obtained in tests on morphine-dependent monkeys and rats (Examples 3 & 4). The successful results obtained with dihydroetorphine in treating heroin and morphine addiction are in sharp contrast to the unreliable results obtained in comparative clinical studies with methadone and other bimodally-acting or mixed agonist-antagonist opioids.

Hence, another aspect of the present invention provides a method of treating opioid addiction by administering a non-addictive opioid or analog thereof, in an amount effective and for a time sufficient to relieve the withdrawal symptoms of opioid addiction and subsequently withdrawing administration of said opioid or analog thereof.

The compounds of the present invention are prepared inter alia by the improved synthetic methods for the preparation of DHE, etorphine and analogs of these compounds as described in U.S. Ser. No. 977,332 filed Nov. 17, 1992. Moreover, the method for preparing salts, particularly pharmaceutically acceptable salts, of the foregoing compounds is also provided therein.

Another aspect of the invention is directed to pharmaceutical compositions containing the opioid compounds of the present invention including dihydroetorphine and its analogues, etorphine and its analogues as well as pharmaceutically acceptable salts of any of the foregoing compounds.

Dosage forms (compositions) suitable for administration can contain from about 10 μg to about 1000 μg of active ingredient per unit. In these pharmaceutical compositions the active ingredient will ordinarily be present in an amount of about 0.5–95% by weight based on the total weight of the composition.

The active ingredient can be administered sublingually in solid dosage forms, such as capsules, tablets, and powders, or be administered parenterally in sterile liquid dosage forms.

Gelatin capsules contain the active ingredient and powdered carriers, such as lactose, sucrose, mannitol, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere.

In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propyl-paraben, and chlorobutanol.

Suitable pharmaceutical carriers are described in *Remington's Pharmaceutical Sciences*, A. Osol, a standard reference text in this field.

Yet another aspect of this invention provides a pharmaceutical composition which comprises a low- or non-addictive opioid analgesic, or a pharmaceutically acceptable salt thereof, in admixture with naloxone which is an opioid antagonist. The low- or non-addictive opioid analgesics are those compounds as provided herein, e.g. etorphine, DHE and the like, in amounts as provided herein. These pharmaceutical compositions are provided in formulations as described above.

The subject compositions are thus useful to avoid diversion or abuse of take-home preparations of solid forms, e.g. tablets of low- or non-addictive opioid analgesics administered orally or sublingually to uses other than detoxification or severe pain relief. Since naloxone has low oral or sublingual bioavailability, an amount of naloxone can be introduced into the preparations that has no effect when taken orally or sublingually but antagonizes the effect of the low or non-addictive opioid analgesic, e.g. DHE, when the preparation is dissolved in water and injected. The amount of naloxone can be readily determined by one of ordinary skill in the art.

The examples serve to illustrate the present invention and are not to be used to limit the scope of the invention.

REFERENCES CITED

Bentley, K. W. & Hardy, D. G.: New potent analgesics in the morphine series. *Proc. Chem. Soc.* p. 220, 1963.

Bentley, K. W. & Hardy, D. G. : Novel analgesics and molecular rearrangements in the morphine-thebaine group. III. Alcohols of the 6,14-endo-ethenotetrahydrooripavine series and derived analogues of n-allylnormorphine and norcodeine. *J. Amer. Chem. Soc.* 89: 3281–3286, 1967.

Blane, G. F. & Robbie, D. S. : Trial of etorphine hydrochloride (M99 Reckitt) in carcinoma pain:preliminary report. *Brit. J. Pharmacol. Chemother.* 20:252–253, 1970.

Blane G. F., Boura, A. L. A., Fitzgerald, A. E. and Lister, R. E.: Actions of etorphine hydrochloride (M99): A potent morphine- like agent. *Brit. J. Pharmac. Chemother.* 30:11–22, 1967.

Casy, A. F. & Parfitt, R. T.: *Opioid Analgesics: Chemistry and Receptors*, Plenum Press, New York, 1986.

Crain, S. M. & Shen, K.-F. : Opioids can evoke direct receptor-mediated excitatory effects on sensory neurons. *Trends Pharmacol. Sci.* 11:77–81, 1990.

Crain, S. M. & Shen, K.-F.: After chronic opioid exposure sensory neurons become supersensitive to the excitatory effects of opioid agonists and antagonists as occurs after acute elevation of GM1 ganglioside. *Brain Res.* 575:13–24, 1992a.

Crain, S. M. & Shen, K.-F. : After GM1 ganglioside treatment of sensory neurons naloxone paradoxically prolongs the action potential but still antagonizes opioid inhibition. *J. Exp. Pharmacol. Ther.* 260:182–186, 1992b.

Crain, S. M., Shen, K.-F. & Chalazonitis, A.: Opioids excite rather than inhibit sensory neurons after chronic opioid exposure of spinal cord-ganglion cultures. *Brain Res.* 455:99–109, 1988.

Deneau, G. A. & Seevers, M. H.: Drug dependence. In: Lawrence D. R., Bacharach, A. L. eds. *Evaluation of Drug Activities: Pharmacometrics.* Vol. 1, London: Academic Press, 1964, pp. 167–179.

Gross, R. A., Moises, H. C., Uhler, M. D. & Macdonald, R. C.: Dynorphin A and cAMP-dependent protein kinase independently regulate neuronal calcium currents. *Proc. Natl. Acad. Sci.* 87:7025–7029, 1990.

Huang, M & Qin, B. Y.: *Acta Pharmacol. Sinica*, 3(1):9, 1982.

Jaffe, J. H.: Drug addiction and drug abuse. in *The Pharmacological Basis of Therapeutics,* 8th ed. (eds. Gilman, A. G., Rall, T. W., Nies, A. S. & Taylor, P.) Pergamon Press, N.Y. pp. 522–573, 1990.

Jasinski, D. R., Griffith, J. D. & Carr, C. B. : Etorphine in man 1. Subjective effects and suppression of morphine abstinence. *Clin. Pharmacol. Ther.* 17:267–272, 1975.

Pasternak, G. W.: *The Opiate Receptors,* Humana Press, New Jersey, 1988.

Shen, K.-F. & Crain, S. M.: Dual opioid modulation of the action potential duration of mouse dorsal root ganglion neurons in culture. *Brain Res.* 491:227–242, 1989.

Shen, K.-F. & Crain, S. M. : Cholera toxin-A subunit blocks opioid excitatory effects on sensory neuron action potentials indicating mediation by Gs-linked opioid receptors. *Brain Res.* 525:225–231, 1990.

Shen, K.-F. & Crain, S. M. : Chronic selective activation of excitatory opioid receptor functions in sensory neurons results in opioid "dependence" without tolerance. *Brain Res.* (in press), 1992.

Wei, E., Loh, H. H. & Way, E. L.: Quantitative aspects of precipitated abstinence in morphine-dependent rats. *J. Pharmacol. Exp. Therap.* 184:398–403, 1973.

W. H. O. Expert Committee on Dependence-Producing Drugs, WHO Tech. Rep. Ser. Vol 343, p. 5, 1966.

Winger, G., Skjoldager, P. & Woods, J. H. : Effects of buprenorphine and other opioid agonists and antagonists on alfantanil- and cocaine-reinforced responding in Rhesus monkey. *J. Pharmacol. Exp. Therap.* 261:311–317, 1992.

EXAMPLE 1

Selective Inhibitory but Not Excitatory Effect of Etorphine and Dihydroetorphine on the Action Potential Duration of Sensory Dorsal Root Ganglion Neurons in Culture Tissue culture:

The experiments were carried out on dorsal root ganglion (DRG) neurons in organotypic explants of spinal cord with attached DRGs (from 13-day-old fetal mice) after 3 to 5 weeks of maturation in culture. The DRG-cord explants were grown on collagen-coated coverslips in Maximow depression-slide chambers. The culture medium consisted of 65% Eagle's minimal essential medium, 25% fetal bovine serum, 10% chick embryo extract, 2 mM glutamine and 0.6% glucose. During the first week in vitro, the medium was supplemented with nerve growth factor (NGF-7s) at a concentration of about 0.5 µg/ml to enhance survival and growth of the fetal mouse DRG neurons.

Electrophysiological recordings:

The culture coverslip was transferred to a recording chamber containing about 1 ml of Hanks' balanced salt solution supplemented with 5 mM $Ca^{2+}$ and 5 mM $Ba^{2+}$ (BSS) to provide a prominent baseline response for pharmacological tests. Intracellular recordings were obtained from DRG perikarya selected at random within the ganglion with micropipette probes. The micropipettes were filled with 3M KCl (resistance about 60–100 megohms) and were connected via a chloridized silver wire to a neutralized input capacity preamplifier (Axoclamp 2A) for current clamp recording. After impalement of a DRG neuron, brief (2 msec) depolarizing current pulses were applied via the recording electrode to evoke action potentials (at a frequency of 0.1 hz). Recordings of the action potentials were stored on a floppy disc using the p-clamp program (Axon Instruments) in a microcomputer (IBM AT-compatible).

Drug test:

Drugs were applied by bath perfusion with a manually operated push-pull syringe system at a rate of 2–3 ml/min. Perfusion of test agents was begun after the action potential and the resting potential of the neuron reached a stable condition during >4 min pretest periods in control BSS. Opioid-mediated changes in the APD were considered significant if the APD alteration was >10% of the control value for the same cell and was maintained for the entire test period (about 5 min). The APD was measured as the time between the peak of the APD and the inflection point on the repolarizing phase.

Figure 1B:
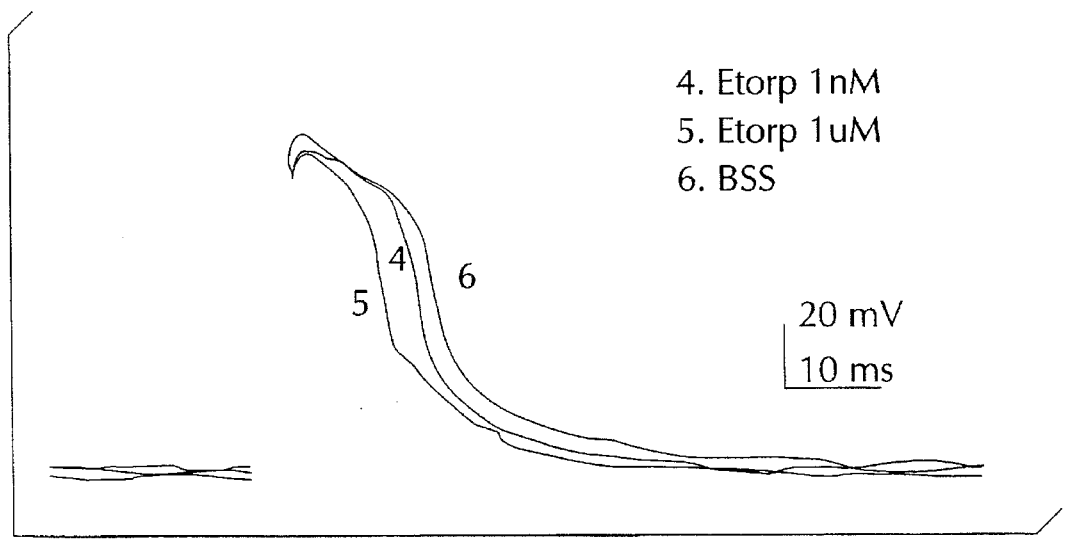
Figure 2:
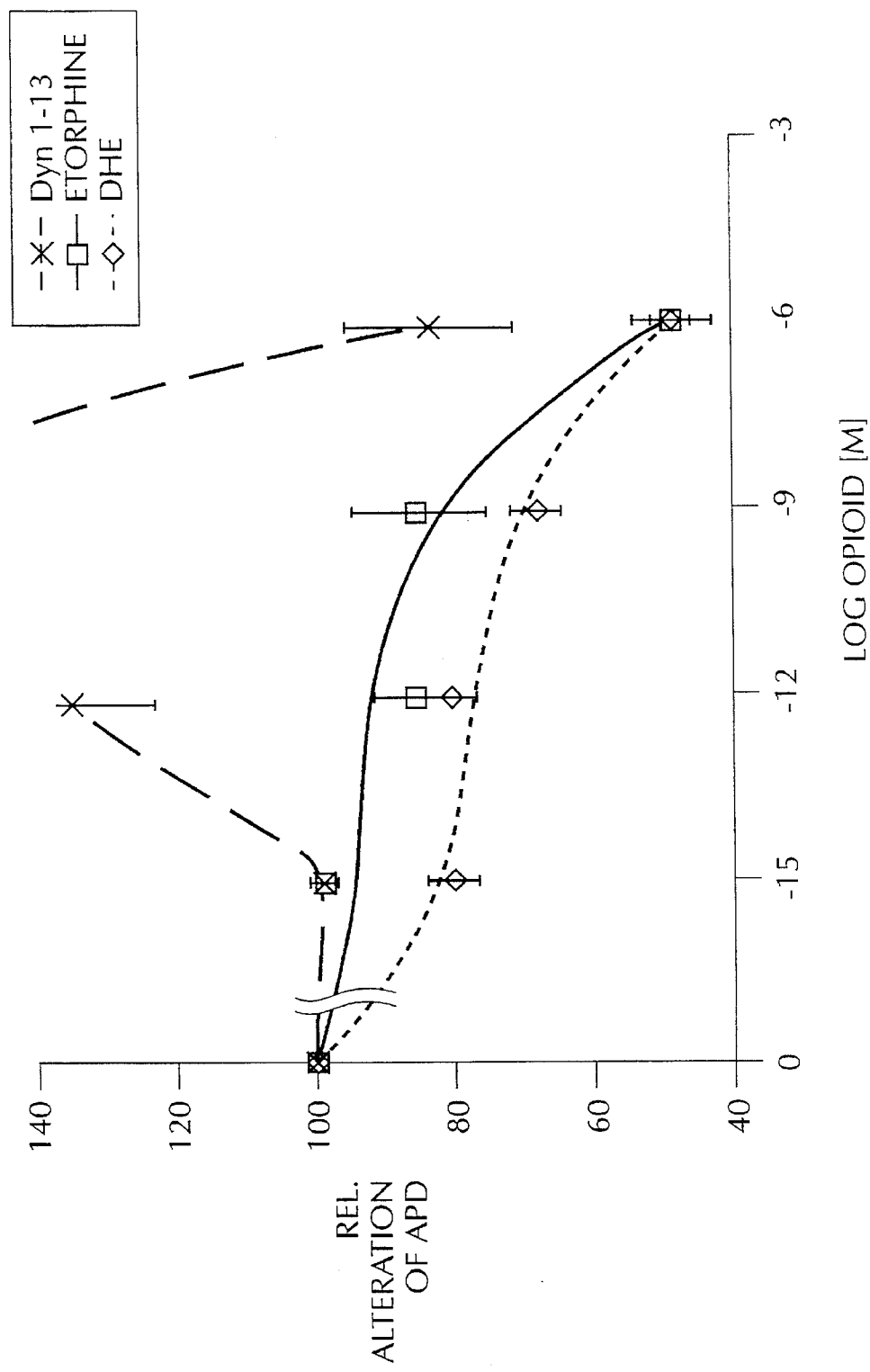
FIG. 2 shows the dose-response relationship of etorphine, DHE and dynorphin (1–13) (Dyn 1–13) effects on the APD of DRG neurons. Etorphine and DHE elicited a dose-dependent shortening of the APD (n=11 and 13, respectively). In contrast, Dyn (1–13) elicited a dose-dependent prolongation of the APD at fM-nM concentrations and required much higher concentrations (ca. μM) to shorten the APD (n=35).

Opioid Responsiveness:

The opioid responsiveness of DRG neurons was analyzed by measuring opioid-induced alterations in the APD of DRG perikarya. DRG neurons in DRG-cord explants were examined for sensitivity to acute application of etorphine or dihydroetorphine at fM to µM concentrations. None of the cells (n=12) showed APD shortening or prolongation in 1 fM etorphine. However, naloxone-reversible APD shortening was observed in 25% of the cells (n=8) after application of pM and nM concentrations of etorphine and in 100% of the cells (n=7) after application of µM concentrations of etorphine (FIGS. 1 and 2). None of the DRG neurons tested with different concentrations of etorphine (n=13) showed APD prolongation.

These results are in sharp contrast to other mu, delta or kappa opioids (e.g. morphine, methadone, DAGO, DPDPE, DADLE, dynorphin (amino acids 1–13) or (amino acids 1–17) and U-50,488H), each of which show bimodal action such that low concentrations (<nM) evoked excitatory APD-prolonging effects and higher concentrations (µM) evoked inhibitory APD-shortening effects on many DRG neurons (FIG. 2; Table 1). For FIG. 2, data were obtained from 11 neurons for etorphine test, half of which were tested with all four concentrations of etorphine (from fM to µM).

Like etorphine, electrophysiologic tests with dihydroetorphine (over fM-µM ranges) on DRG neurons (n=15) showed concentration-dependent inhibitory APD shortening effects, with threshold at fM-pM, and no evidence of excitatory APD prolonging effects (FIG. 2).

TABLE 1

Alteration of action potential duration of dorsal root ganglion neurons treated with high and low concentrations of opioids.

| | Alteration of Action Potential Duration | |
|---|---|---|
| | Opioid at low concentration <nM | Opioid at high concentration µM |
| Morphine | Prolongation | Shortening |
| DAGO | Prolongation | Shortening |
| DADLE | Prolongation | Shortening |
| DPDPE | Prolongation | Shortening |
| U-50,488H | Prolongation | Shortening |
| Dynorphin 1-13 | Prolongation | Shortening |
| Dynorphin 1-17 | Prolongation | Shortening |
| Met-enkephalin | Prolongation | Shortening |
| Leu-enkephalin | Prolongation | Shortening |
| β-endorphin | Prolongation | Shortening |
| Methadone | Prolongation | Shortening |
| Fentanyl | Prolongation | Shortening |
| Levorphenol | Prolongation | Shortening |
| Thebaine | Prolongation | Shortening |
| Etorphine* | Shortening | Shortening |
| Dihydroetorphine* | Shortening | Shortening |

*Selectively activate inhibitory (APD shortening), but not excitatory, opioid receptor-mediated functions.

EXAMPLE 2

Enhanced Inhibitory Effect of Etorphine on Chronic Opioid-Treated, Addicted Sensory Neurons that had become Supersensitive to the Excitatory Effects of Bimodally Acting Opioid Agonists and to Naloxone Drug tests:

Mouse DRG-cord explants, grown for >3 weeks as described in Example 1, were chronically exposed to the bimodally acting (excitatory/inhibitory) delta/mu opioid agonist, DADLE (3 µM) or morphine (1 µM) for 1 week or longer. Electrophysiological recordings were made as in Example 1.

Figure 3A:
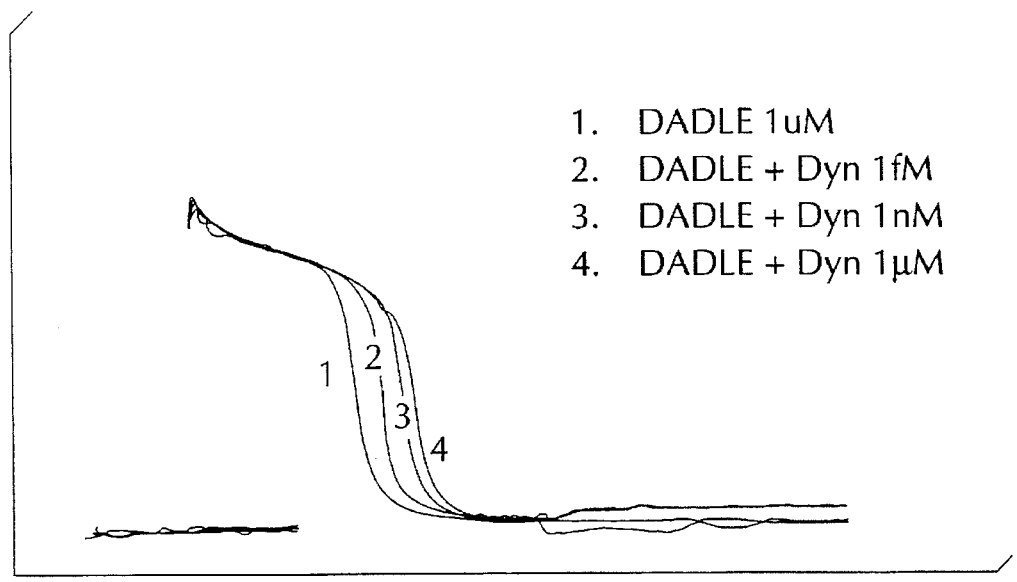
FIG. 3 illustrates that chronic exposure of a DRG neuron to a bimodally acting opioid (DADLE) causes the DRG neuron to become supersensitive to the excitatory effects of dynorphin (1–13) (Dyn), whereas perfusion of etorphine effectively shortened the APD of the same DRG neuron (inhibitory response). 1: Action potential generated by a DRG neuron treated for 3 wks in culture with 1 μM DADLE and then tested in BSS with 1 μM DADLE. 2: APD is prolonged by bath perfusion of 1 fM Dyn with 1 μM DADLE (5 min test). 3,4: APD is further prolonged by sequentially raising the Dyn concentration to 1 nM and 1 μM (5 min tests). 5: Control response 5 min after washout of Dyn with BSS containing 1 μM DADLE. 6: 1 fM etorphine (Etorp) shortens the APD of the same DRG neuron in the presence of 1 μM DADLE. 7–9: Further increases in the concentration of etorphine from 1 pM to 1 μM progressively shorten the APD. 10: APD returns to control value after removal of etorphine.
Figure 3B:
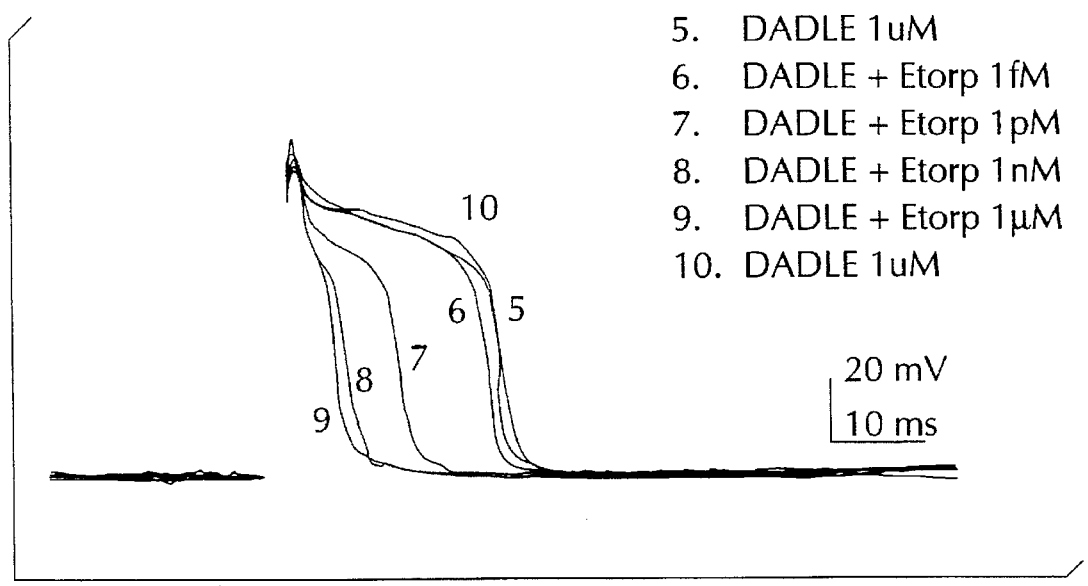

Results:

After such chronic exposure, DRG neurons are supersensitive to the excitatory effects of opioids (Crain & Shen 1992a; Shen & Crain, 1992). Whereas pM-nM Dyn (amino acid 1–13) is generally required to prolong the APD of naive DRG neurons (FIG. 2), fM levels and lower are effective at prolonging the APD after chronic opioid treatment (FIG. 3, traces 1–4). In contrast, acute application of etorphine to chronic DADLE-treated neurons effectively shortened the APD of the same DRG neurons that showed supersensitive excitatory responses to low concentrations of bimodally-acting opioids (FIG. 3, traces 6–9). Furthermore, the inhibitory APD-shortening effect of etorphine on DRG neurons appears to be significantly enhanced. While pM etorphine was effective in shortening the APD of 25% of the DRG neurons tested in naive explants (FIGS. 1 and 2), this low opioid concentration was effective in all of the chronic DADLE-treated DRG neurons tested in the presence of 1 µM DADLE (n=4; FIG. 3, traces 5 and 6). This same low concentration of etorphine (pM) was effective in 71% of the chronic morphine-treated (1 µg/ml) DRG neurons tested in the presence of 1 µg/ml morphine (n=7). Dose response tests on chronic DADLE-treated DRG neurons showed, in fact, that the magnitude of the APD was progressively shortened when the acute etorphine concentration was increased sequentially from 1 fM to 1 µM (FIG. 3, traces 6–9).

Figure 4:
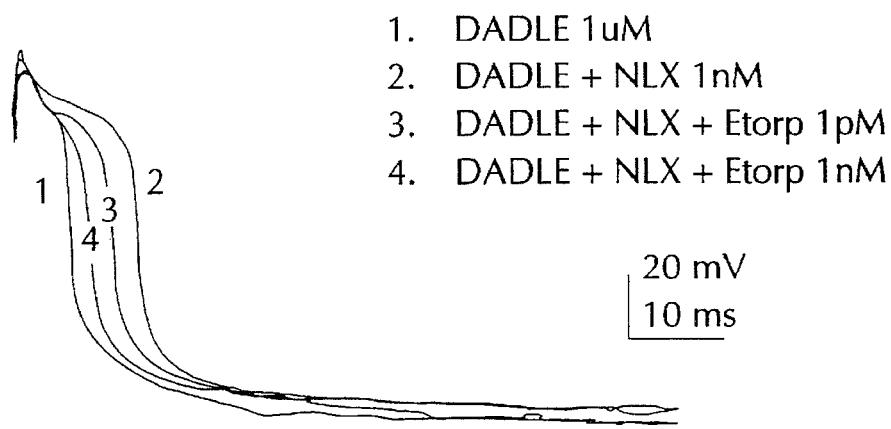
FIG. 4 shows that chronic exposure to a bimodally acting opioid (DADLE) followed by acute application of low concentrations of etorphine can block the excitatory APD-prolonging effects precipitated by naloxone (NLX) in this supersensitive DRG neurons. 1: Action potential generated by a DRG neuron treated for 2 wks in culture with 1 μM DADLE and then tested in BSS with 1 μM DADLE. 2: 1 nM NLX prolongs the APD of this DRG neuron (5 min test). In contrast, nM naloxone is ineffective on naive DRG neurons (Crain & Shen, 1992a,b) 3: Acute addition of 1 pM etorphine attenuates the naloxone-induced APD prolongation (5 min test). 4: Further increase in concentration of etorphine to 1 nM almost completely blocks the naloxone-induced APD prolongation.

The opioid antagonist, naloxone (nM-µM), does not alter the APD of naive DRG neurons (Crain & Shen 1992a, b). In contrast, after chronic opioid, such as DADLE treatment, acute application of low concentrations of naloxone prolongs the APD of sensory neurons (Crain et al, 1992b; Shen & Crain, 1992). The naloxone-induced excitatory APD-prolonging effect on chronic opioid-treated DRG neurons is shown in FIG. 4, traces 1 and 2. Acute application of low concentrations of etorphine effectively blocks the naloxone-induced APD prolongation of DRG neurons (n=3; FIG. 4, traces 3 and 4) whereas bimodally acting opioids are ineffective.

Since etorphine and dihydroetorphine elicit potent inhibitory effects on naive sensory neurons even when applied at extremely low (pM) concentrations and show no signs of concomitantly activating excitatory opioid receptors on these cells, these in vitro electrophysiologic analyses predict that application of etorphine and dihydroetorphine in vivo at the relatively low doses required to produce analgesia (<1, 000 times lower than morphine) are not addictive even after sustained application for treatment of chronic pain.

EXAMPLE 3

Suppression of Withdrawal Symptoms by DHE in Morphine-Dependent Rats

Morphine-dependent rat model:

Wistar rats of both sexes, 120–150 g body weight, were administered morphine subcutaneously (s.c.) twice a day (8:00 a.m., 4:00 p.m.) starting at a dose of 20 mg/kg/day, with an increment of 20 mg/kg/day for 5 consecutive days until the final dose reached 100 mg/kg/day.

Naloxone (NLX) precipitation for the scoring of withdrawal symptoms:

3–4 hrs after administering the last dose of morphine (or other test drug (s)), withdrawal symptoms of morphine-dependent rats were precipitated by intraperitoneal (i.p.) injection of naloxone (4 mg/kg). Naloxone-induced withdrawal symptoms were monitored for 1 hr thereafter and scored according to the method of Wei et al, 1973.

Animal groups:

After 5 days of morphine addiction, the animals were divided into 7 groups according to Table 2. Each group contained 5–6 rats.

Groups 1, 2, and 3 received 20 mg/kg morphine (4 times the $ED_{50}$ for analgesia), 9 mg/kg methadone (9 times the $ED_{50}$ analgesia) or 6 µg/kg DHE (12 times the $ED_{50}$ analgesia) by i.p. injection, respectively. These opioid agonists were injected 15–30 min before naloxone precipitation was initiated. After the naloxone withdrawal test was completed, groups 1, 2, and 3 were continued on morphine 100 mg/kg (s.c.) for another 4 consecutive days. A second naloxone precipitation test was given on the 4th day but only saline was administered (i.p.) prior to naloxone.

The first naloxone precipitation test was performed on the animals of groups 4, 5, and 6 in the same manner as for groups 1–3, except the administration of opioid agonists 15–30 min prior to the naloxone test. For the second naloxone test, groups 4, 5 and 6 received 100 mg/kg morphine (s.c.) twice a day, 3 µg/kg DHE 4 times a day, or 6 mg/kg methadone, 4 times a day, instead of morphine at 100 mg/kg, for 4 days, respectively. The second naloxone test was performed as above on the 4th day.

After the first naloxone precipitation test, Group 7 animals were given saline (s.c.) as control for 4 days before the second naloxone test.

The body weight of the animals was monitored during the entire period.

Results:

One to 2 min after intraperitoneal injection of naloxone, the morphine-dependent rats began to show naloxone induced withdrawal symptoms with a peak response occurring within 15 min. An hour later the body weight of the animals was greatly reduced. Intraperitoneal injection of morphine (20 mg/kg), DHE (6 µg/kg) or methadone (9 mg/kg) prior to the administration of naloxone suppressed the naloxone induced withdrawal symptoms of the rats. No significant differences in suppressing effect were detected among these three opioid substitutes. For morphine, DHE and methadone, prevention of body weight loss was 43.5%, 49.8% and 48.15%, respectively, and suppression of other withdrawal symptoms was scored as 45.5%, 63.7% and 49.4%, respectively.

After naloxone precipitation, the body weight of the dependent rats continued to decrease. The loss of body weight reached its maximum 24 h after naloxone precipitation. A gradual weight recovery was achieved by 90 h.

Figure 5:
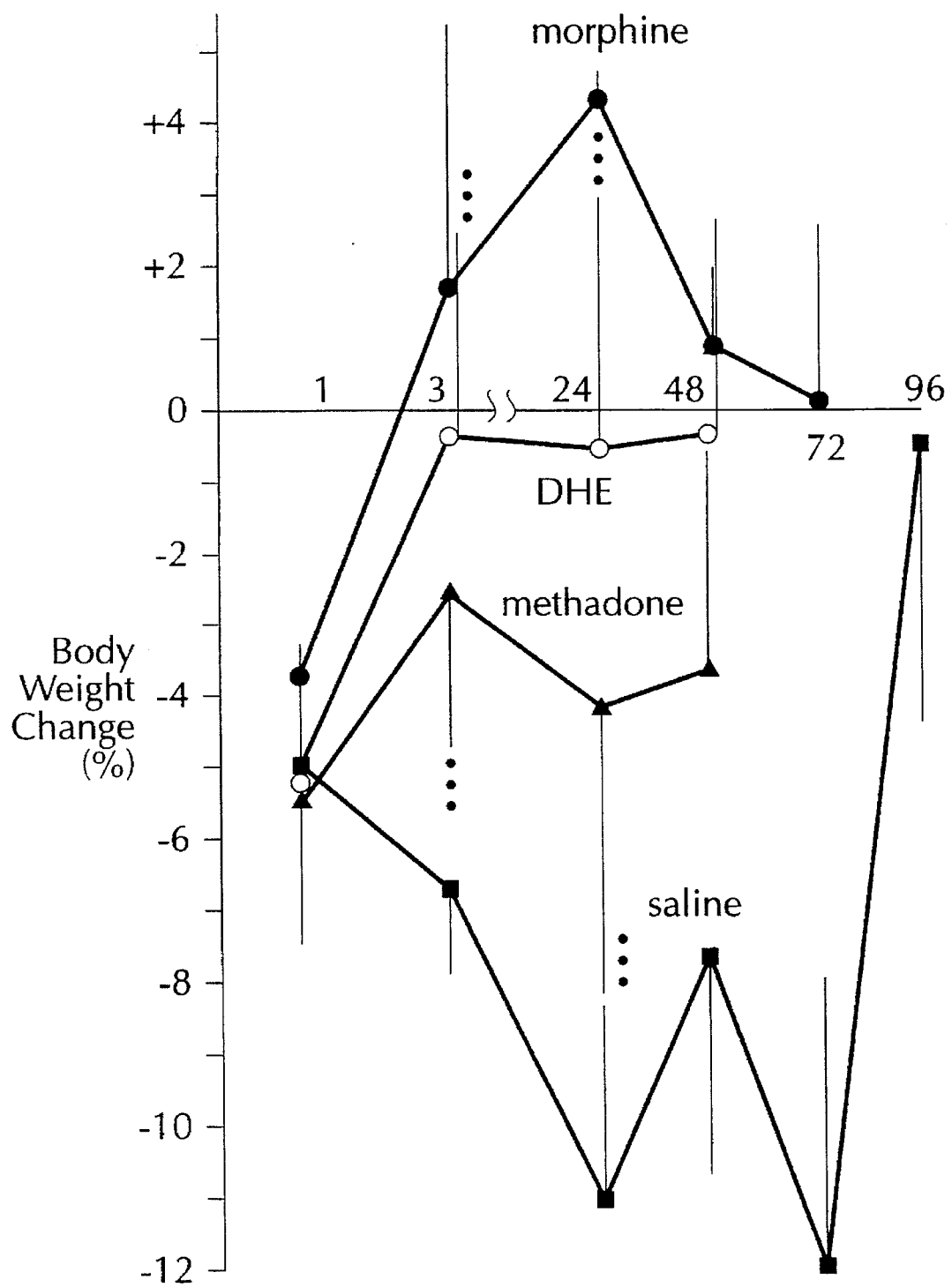
FIG. 5 illustrates the relief of naloxone-precipitated, sustained body weight loss by morphine, DHE and methadone injections in morphine-dependent rats. Daily dose: morphine 100 mg/kg, divided into 2 subdoses; DHE 12 μg/kg, divided into 4 subdoses; methadone 24 mg/kg, divided into 4 subdoses. Filled circle: morphine group; open circle: DHE group; filled triangle: methadone; cross: saline control group. X±SD, ***p<0.01, as compared with saline control group.

Subcutaneous injection of morphine, DHE or methadone was given for several days after the first naloxone precipitation test. The loss of body weight of morphine-dependent rats was found to be reduced in all three groups treated with opioid agonists. Subcutaneous administration of morphine (one hour after naloxone precipitation) reversed the body weight loss in 3 hours, with occasional weight gain in some of the rats. A complete recovery of weight loss was observed 48 h later. The effect of subcutaneous injection of DHE or methadone on body weight loss was not as dramatic as with morphine. However, both opioids did prevent further body weight loss. When compared with the untreated control group (saline injected), the effect of both DHE or methadone on body weight loss was highly significant (FIG. 5).

Figure 7:
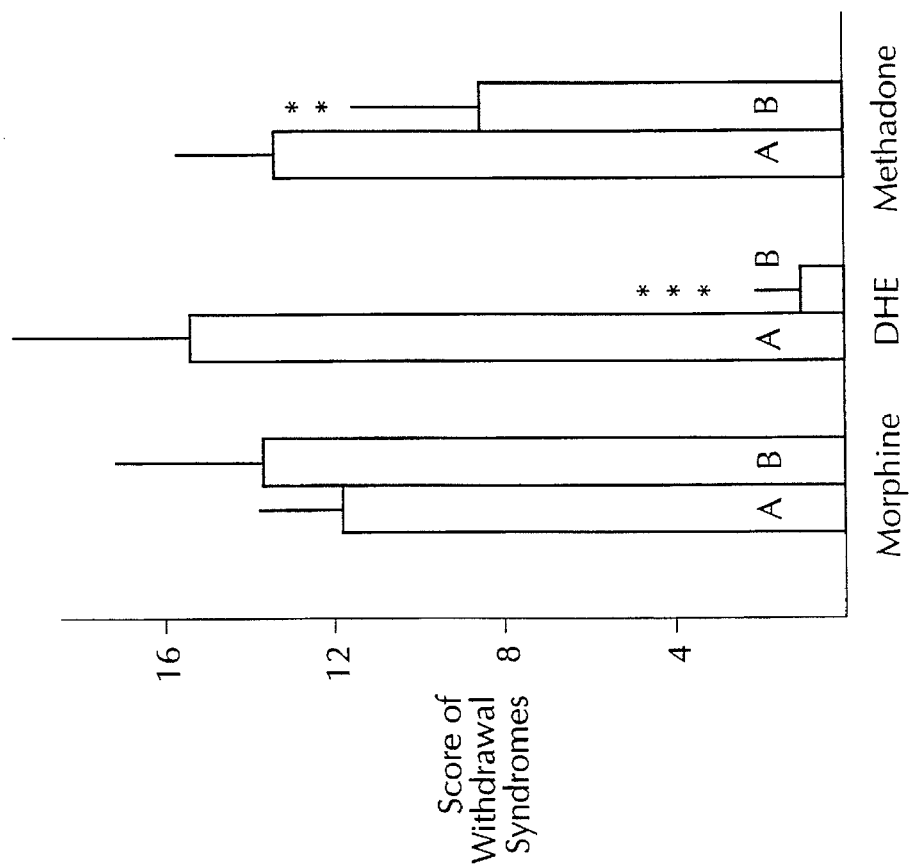
FIG. 7 depicts the withdrawal symptom scores after naloxone precipitation for DHE and methadone substitution in morphine-dependent rats. Rats were treated as described in FIG. 6. Column A: Withdrawal scores from the first naloxone precipitation test. Column B: Withdrawal scores from the second naloxone precipitation test. Statistical p values between the first and second naloxone precipitation test are "", p<0.05 and "*", p<0.01. The p value for the DHE group relative to the methadone group is p<0.01.
Figure 6:
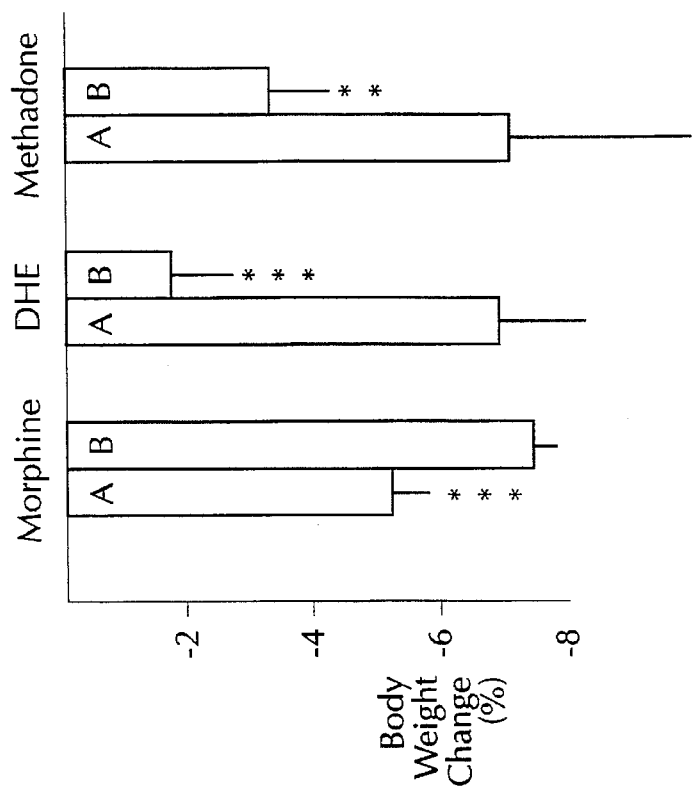
FIG. 6 depicts the effect of DHE and methadone substitution on naloxone precipitated body weight loss is morphine-dependent rats. The body weight loss from the first naloxone precipitation test is provided in Column A. The second naloxone precipitation test was performed after 4 days of maintaining one group of rats with morphine (100 mg/kg/day, divided into 2 subdoses), a second group with DHE (12 μg/kg/day, divided into 4 subdoses) and a third group with methadone (24 mg/day, divided into 4 subdoses). The body weight loss after the second naloxone precipitation test is provided in Column B. Statistical p values between the first and second naloxone precipitation test are "", p<0.05 and "*", p<0.01. The p value for the DHE group relative to the methadone group is p<0.05.

After the first naloxone precipitation test, some of the animals continued to be maintained on morphine (s.c.). Four days later, a second naloxone test was given. The second naloxone test resulted in more severe withdrawal symptoms relative to the first test. In contrast, in those animals that were treated with DHE (s.c., 4 days) instead of morphine, the second naloxone test failed to precipitate any withdrawal symptoms except minor loss in body weight. In the animals maintained with methadone (s.c., 4 days), the second naloxone injection precipitated less severe withdrawal symptoms in comparison to the morphine group, yet more severe when compare with the DHE group (FIGS. 6 and 7).

TABLE 2

Animal Groups Used to Test the Suppression of NLX-induced Withdrawal Symptoms by Different Opioids

| Animal Groups | Development of Morphine Dependence 5 days | Pretreatment (15–30' prior to 1st test) | 1st NLX Test | Continued Maintenance with Opioids 4 days | Pretreatment (15–30' prior to 2nd test) | 2nd NLX Test |
|---|---|---|---|---|---|---|
| 1 | Morphine 20→100 mg/kg | Morphine (20 mg/kg) | NLX | Morphine 100 mg/kg | Saline | NLX |
| 2 | Same as 1 | Methadone (9 mg/kg) | NLX | Same as 1 | Saline | NLX |
| 3 | Same as 1 | DHE (6 µg/kg) | NLX | Same as 1 | Saline | NLX |
| 4 | Same as 1 | — | NLX | Morphine 50 mg/kg | — | NLX |
| 5 | Same as 1 | — | NLX | DHE 3 µg/kg | — | NLX |
| 6 | Same as 1 | — | NLX | Methadone 6 mg/kg | — | NLX |
| 7 | Same as 1 | — | NLX | Saline | — | NLX |

EXAMPLE 4

Anti-Addictive Effects of DHE Treatment of Morphine-Dependent Monkeys

Morphine-dependent monkey model:

Seven male rhesus monkeys (*Macaca mulatta*, 3.4–5 kg) were injected with morphine (s.c.) twice a day (8:00 a.m., 4:00 p.m.), startling at a dose of 10 mg/kg/day and increasing the dose by increments of 5 mg/kg/day every third day until the dosage reached 50 mg/kg/day on the 24th day. This dosage was continued for another 10 days prior to performing drug tests.

Stage 1 drug tests:

The monkeys were randomly divided into 2 groups. At 24 h after withdrawal of morphine, Group A (4 animals) received 3 µg/kg DHE (s.c.) every 3 h. The interval between DHE administration was increased gradually so that by the 3rd day, DHE was only given twice a day, and then stopped for 2 days of observation. Group B (3 animals) was treated the same manner as group A except, this group received saline instead of DHE. After completion of these tests, all the animals were treated with morphine for 12 consecutive days by administration of 50 mg/kg/day morphine (s.c.) twice a day. The test was repeated except the Group A monkeys received the saline controls and the Group B monkeys received the DHE treatment. Withdrawal symptoms of the animals were observed and scored according to Deneau & Seevers (1964), during the entire experimental period.

Figure 8:
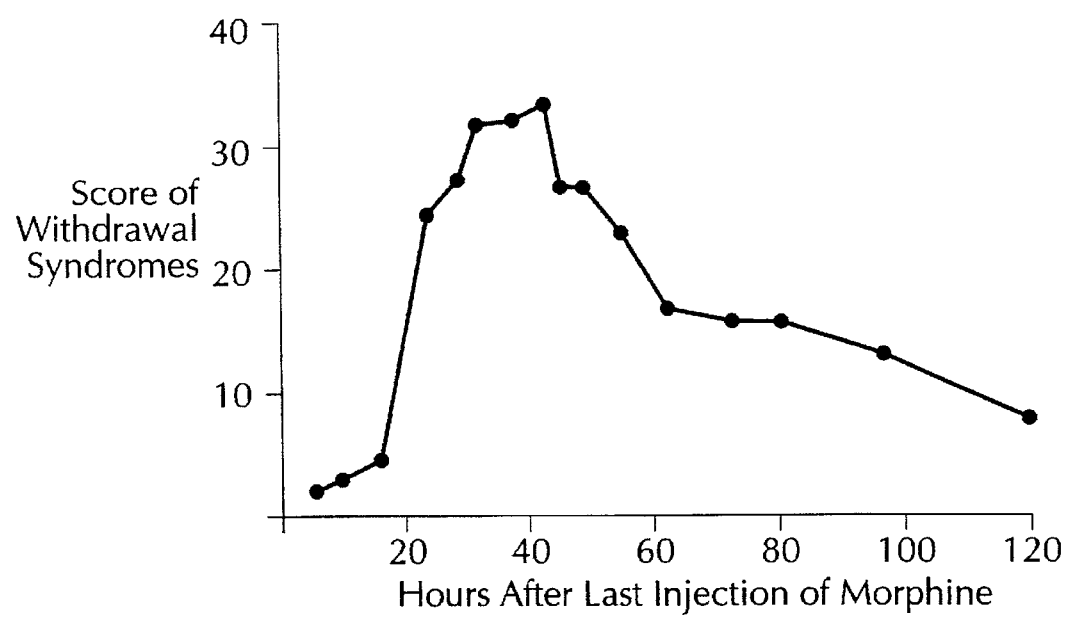
FIG. 8 shows the development of withdrawal symptoms in morphine-dependent monkey after cessation of morphine.

Sixteen hours after withdrawal of morphine, withdrawal symptoms began to appear in the morphine-dependent monkeys. Symptoms were moderate at first and included yawning, salivation, agitation and fear. These signs became more severe as time went on. Within 20–60 h after withdrawal of morphine, the animals' withdrawal symptoms included vomiting, tremor, teeth-gritting on chain, eye closing, lying on its side and dyspnea. All these symptoms are indicative of extreme agitation. After 60 h these symptoms gradually subsided. By 120 h after withdrawal of morphine, some moderate withdrawal symptoms were still detected (FIG. 8). One week later all the withdrawal symptoms had disappeared.

Figure 9:
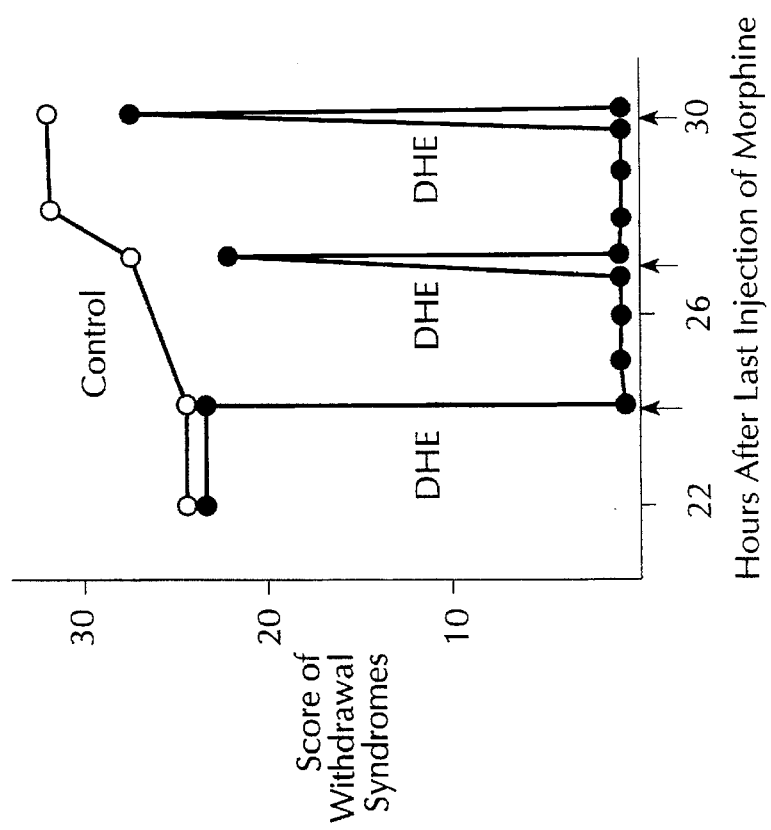
FIG. 9 illustrates the relief of withdrawal symptoms by DHE in morphine-dependent monkeys. The arrows indicate time of DHE injection (3 μg/kg). Open circle: control group; filled circle: DHE group.

In sharp contrast, all of these withdrawal symptoms were completely suppressed by DHE one minute after its administration (3 µg/kg, s.c.). Two and a half to three hours later, withdrawal symptoms reappeared which were again suppressed by another dose of DHE (FIG. 9). This suppressing effect of DHE on morphine withdrawal symptoms was observed with each monkey. DHE continued to be effective at suppressing withdrawal symptoms for 3–4 days with repeated injections at 2.5–3 h intervals. Discontinuation of DHE injection at 80 h after morphine withdrawal did not trigger any withdrawal symptoms, indicating that the animals had not become dependent on DHE during this substitution treatment.

Stage 2 drug tests:

After the stage 1 experiments, all 7 monkeys were administered morphine (s.c.) at a dose of 50 mg/kg/day for 7 days. The morphine-addicted monkeys were then randomly divided into 3 groups. Group 1 was maintained with s.c. injection of 25 mg/kg morphine twice a day for 9 days. Group 2 was substituted with DHE by s.c. injection of 3 µg/kg DHE (equi-analgesic dose) four times a day for 4 days, of 1.5 µg/kg DHE three times a day for 2 days and then twice a day for 3 days. Group 3 was substituted with methadone by s.c. injection of 6 mg/kg methadone (equi-analgesic dose) four times a day for 4 days, of 3 mg/kg three times a day for 2 days and then twice a day for 3 days.

Sixteen hours after the last injection of opioid, each animal was precipitated with naloxone (1 mg/kg, s.c.) to evaluate the severity of naloxone withdrawal symptoms for 1 day. Seven days later, another naloxone precipitation test was performed on these monkeys for 1 day. After completion of all tests, 3 monkeys were randomly selected for morphine addiction (25 mg/kg, s.c., twice a day for 7 days). Naloxone precipitation tests were performed twice on these 3 monkeys, the first trial given after the last injection of morphine and the second trial given 7 days thereafter.

Since the action period of DHE and methadone is relatively short, some moderate withdrawal symptoms appeared during the 6 hr intervals between injections on the first 3 days. After these 3 days, the withdrawal symptoms became milder and gradually disappeared.

Naloxone precipitation tests were carried out after 9 days of substitution treatment with DHE or methadone. For the monkeys maintained on morphine, naloxone injection precipitated a series of withdrawal symptoms after 15 sec. These symptoms included squeaking, coughing, rolling, tremor, vomiting, agitation, teeth-gritting on chain, dyspnea, and finally lying down on the ground. The animals recovered by 7 days later. The monkeys substituted with methadone showed moderate naloxone withdrawal symptoms including yawning, placing hands on the belly, tremor of extremities, frequent teeth-gritting on chain and agitation. However, those animals substituted with DHE showed no change in behavior both before and after naloxone precipitation. Table 3 shows the scores of naloxone withdrawal symptoms from the 3 different groups of monkeys. Once morphine was fully excreted from the body (7 days after withdrawal), naloxone no longer precipitated any withdrawal symptoms.

The naloxone precipitation test was used to evaluate whether these animals were dependent on morphine or had become dependent on the substitution opioid.

Figure 10:
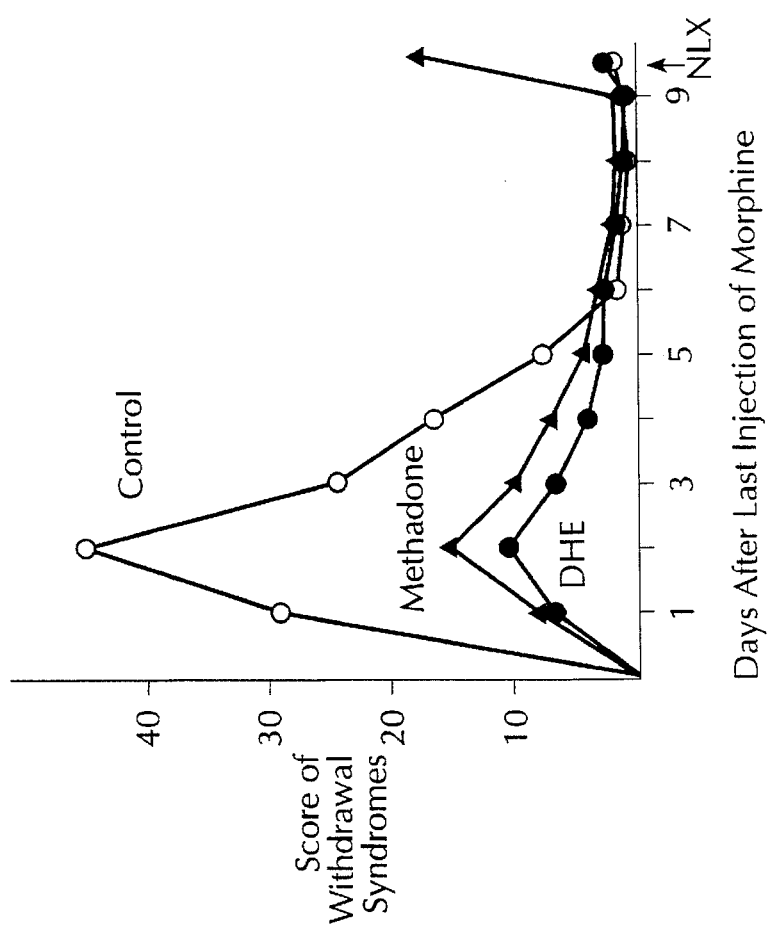
FIG. 10 illustrates the therapeutic effect of DHE and methadone on withdrawal symptoms of morphine-dependent monkeys. The arrows indicate the time of naloxone (NLX) precipitation (1 mg/kg). Open circle: control group; filled circle: DHE group; filled triangle: methadone group.

FIG. 10 illustrates the variations in the scores of withdrawal symptoms in monkeys after DHE or methadone substitution relative to compulsive withdrawal. In the compulsive withdrawal group (upper trace) withdrawal symptoms reached a maximal score during the first several days, but returned to zero by 7 days after abrupt morphine withdrawal. On day 9, naloxone no longer precipitated any withdrawal symptoms. For the methadone substitution group (middle trace), the withdrawal symptoms during the first several days were partially suppressed. On day 9, naloxone precipitated withdrawal symptoms, suggesting that the animals have already switched to methadone dependence. For DHE substitution group (lower trace) only minor withdrawal symptoms were observed. Naloxone precipitation tests on day 9 did not trigger any withdrawal symptoms. These results indicate that DHE is an ideal low- or non-addictive substitution drug for treatment of opioid abstinence problems.

TABLE 3

Scores of naloxone withdrawal syndromes in morphine dependent monkeys with or without DHE or methadone substitution treatment

| Treatment[a] (n) | Scores of withdrawal syndromes ($\bar{X} \pm SD$) | |
| --- | --- | --- |
| | 1st naloxone precipitation[b] | 2nd naloxone precipitation[c] |
| morphine (4) | 49.0 ± 2.2 | 1.5 ± 1.0 |
| DHE (3) | 2.0 ± 1.0*** | 1.0 ± 1.0 |
| methadone (3) | 17.0 ± 4.6*** | 1.3 ± 1.2 |

[a]Daily treatment dosages were 50 mg/kg morphine (divided into 2 subdoses), 12 µg/kg DHE (divided into 4 subdoses) decreased to 3 µg/kg (divided into 2 subdoses), and 24 mg/kg methadone (divided into 4 subdoses) decreased to 6 mg/kg (divided into 2 subdoses).
[b]The first naloxone precipitation test was performed 16 h after the last injection of opioid.
[c]The second naloxone precipitation test was performed 7 days after the last injection of opioid.
***$p < 0.01$, compared to the morphine group. For the DHE group compared to the methadone group, then $p < 0.01$.

EXAMPLE 5

DHE Elicits Potent Low- or Non-Addictive Analgesia in Acute and Chronic Pain Patients The results in the first stage clinical trial showed that none of the 20 volunteers had euphoria feeling after DHE administration through sublingual route at 60 µg single dose. At high dosage (e.g. >1 mg per day), dizziness, nausea, vomiting and lethargy appeared. The results from second stage clinical trial demonstrated that DHE can effectively relieve postoperative pain and pain caused by terminal stage of cancer. The effective rate of 730 cases that have complete medical records was 97.6%. Among them, the effective rate of acute pain in patients from departments of surgery, obstetric and gynecology approached nearly 100%. The effective rate for relief of chronic severe pain and terminal stage of cancerous pain was 90–95%. The clinical data indicate that the analgesic effect of DHE is substantial with only mild side effects. DHE treatment was effective in those terminal stage cancer patents that were unresponsive to morphine or pethidine (demerol) treatment. No cross tolerance to DHE was found in these patients. Long-term use of DHE can result in tolerance; however, the degree of tolerance is less than that observed with morphine or pethidine.

Clinical treatment with DHE has been conducted in more than one hundred thousand patients in China. As an analgesic, the main disadvantage of DHE is its short action period (about 3–4 hours). Compared with morphine, DHE has high analgesic effect and low addictivity, whereas morphine has relatively low analgesic effect and high addictivity. During many years of trials using DHE as an analgesic, no cases of drug abuse were ever reported. This phenomena may be attributed to the strict regulation of DHE treatment. The medication period for ordinary pain is typically limited to 1 week; whereas, for patients with terminal cancer pain, the treatment period is much longer. Although some of the patients became tolerant to DHE after long-term use, there is a slight chance that a few patients may become addicted to the drug after long-term use (e.g., >6 months).

EXAMPLE 6

DHE Substitution Treatment Suppresses Withdrawal Symptoms in Opiate Addicts without Concomitant DHE Addiction General protocol:

Institution of DHE therapy as a substitute drug began with a sufficient dose on days 1–3 to suppress completely the withdrawal symptoms. On days 4–7, the dosage was reduced and by days 8–10 the DHE substitution therapy was terminated. This protocol was followed because (1) withdrawal symptoms are most severe during the first 3 days after abrupt withdrawal of heroin or other addictive opioid; (2) withdrawal symptoms gradually decline and disappear after 7–10 days; and (3) consecutive use of DHE as a substitution agent for 7–10 days does not produce any self-dependence.

DHE administration:

More than 300 cases of chronic heroin users were treated for 7–10 days with DHE in 10 hospitals in China. DHE was administered either sublingual in tablet form (40 µg) or by intramuscular injection (20 µg) or by intravenous dripping (20 µg). The tablet form was used more often. At the onset of withdrawal symptoms, sublingual administration of 1–2 tablets (20–40 µg) of DHE effectively suppressed the symptoms. Sustained suppression of withdrawal symptoms required repeated DHE medication every 2–4 h. Total dosage, was adjusted according to the severity of the withdrawal symptoms. Typically after 4 days of DHE medication, the dosage required to suppress withdrawal symptoms was generally reduced. The entire course of DHE substitution was generally 7 days. (In one instance of overdose of DHE, respiratory side effects occurred.)

For addicts whose withdrawal symptoms were so severe and violent that sublingual medication was not enough to subdue them, intramuscular injection of DHE (20 µg) gave instant relief. The addict generally became quiet and cooperative. However, to maintain the therapeutic effect, it was necessary to administer DHE by intravenous dripping (100 µg in 500 ml glucose saline for 6–10 hr). The transfusion rate depended upon the severity of symptoms: the drip rate was increased when the patient showed sign of restlessness or decreased when the patient was quiet and complained of lethargy. In severe cases, intravenous transfusion of DHE was maintained for 3–4 days with progressive decrease in dosage. On day 4 or 5, intravenous dripping of DHE was converted to sublingual DHE administration and terminated on day 7. Occasionally treatment was prolonged to 8–9 days, but never more than 10 days to prevent possible occurrence of dependence. Hence, by using this optimal 7–10 day treatment period DHE is effectively employed as a substitute for drug addiction therapy.

The effectiveness of DHE substitution therapy was evaluated on day 10 by the naloxone precipitation test (0.4–0.8 mg naloxone, intramuscular injection) and urine analysis of the residual amount of opioid. The treatment course was considered successful if both tests were negative.

One of the primary advantages of DHE over methadone substitution therapy is the early onset of DHE effectiveness. Withdrawal symptoms were markedly relieved after 10–20 min of sublingual administration or 5 min of intramuscular injection of DHE. In contrast, with methadone substitution the first dose usually begins at 10 mg and is increased every hour until the therapeutic effect is achieved. Such treatment can last from one to several hours before symptomatic relief. This period is intolerable to a patient with severe withdrawal symptoms. Furthermore, methadone substitution therapy often results in the rebound of withdrawal symptoms, suggesting dependence on methadone.

In contrast, cessation of DHE administration generally proceeded smoothly. As with methadone, the side effects of DHE were negligible during substitution treatment for drug addiction. Since DHE is short acting (only 2–4 hr), frequent administration may be necessary. To avoid this, intravenous dripping of DHE is recommended. However, intravenous administration can only be prescribed in the hospital and is not applicable to the ordinary drug rehabilitation clinic. Since methadone is effective orally (once or twice a day), one alternative is to combine DHE and methadone treatments. For example, DHE is used initially for swift control of the withdrawal symptoms and is then replaced by methadone to maintain the suppressing effect for 2–3 days. The treatment is then switched back to DHE on a decreasing dosage regime until DHE is no longer needed (usually another 5–10 days). This combined therapy is safe, pragmatic and convenient.

EXAMPLE 7

Preparation of Various Dihydroetorphine (DHE) Salts and Analysis of Duration and Potency of the Analgesic Effects Thereof A total of 26 dihydroetorphine (DHE) salts were prepared according to step (e) of Example 7 of U.S. Ser. No. 977,332, filed Nov. 17, 1992 except the various acids listed below were substituted for HCl.

I. Structures of 26 acids employed to form derivatives of dihydroetorphine salts

COOH  
|  
COOH                                *1.

CH$_2$COOH  
|  
CH$_2$COOH                          *2.

CH$_3$COOH                           *3.

-continued

HO—CH—COOH  
|  
CH$_2$COOH                          4.

CH$_3$CHCOOH  
|  
OH                                   5.

HO—CH—COOH  
|  
HO—CH—COOH                          6.

CH$_2$COOH  
|  
HO—C—COOH  
|  
CH$_2$COOH                          *7.

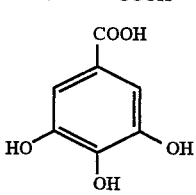                 8.

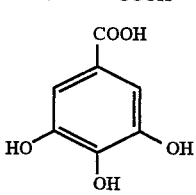                 9.

HCCOOH  
||  
HCCOOH                               *10.

CH$_2$CH=CHCH=CHCOOH                 11.

CH$_3$(CH$_2$)$_{10}$COOH           12.

CH$_3$(CH$_2$)$_{14}$COOH           13.

CH$_3$(CH$_2$)$_{16}$COOH           14.

C$_6$H$_5$CH(OH)COOH                *15.

(C$_6$H$_5$)$_2$C(OH)COOH           *16.

C$_{76}$H$_{52}$O$_{46}$            17.

C$_6$H$_5$CHCOOH  
|  
CH$_2$OH                            18.

C$_6$H$_5$SO$_3$H                   19.

H  OH H  
HOH$_2$CC—C—C—C—COOH  
        O  H  OH                    20.

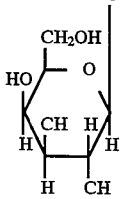

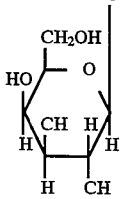               21.

CH$_3$CHCOOH  
|  
OH                                  22.

C$_6$H$_4$(NH$_2$)(SO$_3$H)         23.

HBr                                 *24.

-continued

 *25.

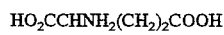 *26.

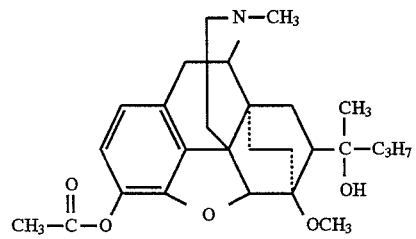 27.

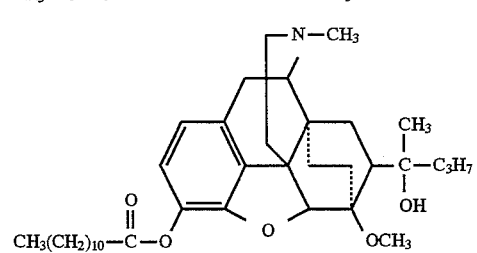 28.

*Preliminary screening tests have been done.

A "mouse hot plate" (55° C.±0.5° C.) method as previously described (Huang and Qin, 1982) was used to score % analgesia to measure the potency of each DHE salt which was injected to animals subcutaneously. The $ED_{50}$ (the dose that gives rise to 50% analgesia as calculated by the following formula) was measured for the DHE salts shown in Table 4.

$$\text{Analgesia \%} = \frac{\text{Pain threshold (sec) after administration} - \text{Pain threshold (sec) before administration}}{60 - \text{Pain threshold (sec) before administration}}$$

A dose of 5 $ED_{50}$ was used for each salt to measure the corresponding analgesic duration. "Analgesia %" was recorded at 90, 120 and 150 min after administration (Table 5).

In summary, an $ED_{50}$ (μg/kg) in time range of 0.50 to 2.0 was observed with the 12 DHE salts tested, indicating an equivalent level of analgesic effect: conferred by these salts (see data presented in Table 4). Furthermore, except for acetyl DHE, DHE maleate, and DHE amygdalate, all DHE salts demonstrated an equivalent level of analgesia over a 120–150 min duration.

TABLE 4

Analgesic Effect of Various DHE Salts

| Salts of DHE* | $ED_{50}$ (μg/Kg) |
|---|---|
| DHE hydrochloride | 1.43 |
| Acetyl DHE (27) | 0.47 |
| DHE maleate (10 | 0.58 |
| DHE succinate (2) | 0.83 |
| DHE oxalate (1) | 0.68 |
| DHE acetate (3) | 0.51 |
| DHE malate (4) | 0.62 |
| DHE asparagate (25) | 1.12 |
| DHE glutamate (26) | 0.65 |
| DHE amygdalate (15) | 0.61 |
| DHE dibenzoylhydroxyl acetate (16) | 1.29 |
| DHE citrate (7) | 1.73 |

*The numbers following each salt correspond to the numbered compounds of Example 7

TABLE 5

| Salts of DHE | Analgesia % (x ± SD) | | |
|---|---|---|---|
| | 90 min | 120 min | 150 min |
| DHE hydrochloride | 42.39 ± 31.34 | 20.05 ± 10.91 | 28.49 ± 14.21 |
| Acetyl DHE | 5.96 ± 12.65 | 8.85 ± 9.47 | ND |
| DHE maleate | 15.84 ± 13.82 | ND | ND |
| DHE succinate | 26.16 ± 14.86 | 30.77 ± 42.35 | 32.26 ± 35.89 |
| DHE oxalate | 14.21 ± 6.37 | 19.35 ± 24.14 | ND |
| DHE acetate | 21.64 ± 10.11 | 29.54 ± 30.93 | ND |
| DHE malate | 26.92 ± 23.75 | 22.36 ± 19.29 | ND |
| DHE asparagate | 40.96 ± 37.28 | 35.94 ± 45.06 | 21.44 ± 35.68 |
| DHE glutamate | 29.33 ± 36.15 | 9.27 ± 12.57 | 14.09 ± 17.07 |
| DHE amygdalate | 29.15 ± 26.73 | 1.87 ± 2.97 | ND |
| DHE dibenzoylhydroxyl acetate | 45.01 ± 49.66 | 13.85 ± 17.49 | ND |
| DHE citrate | 56.12 ± 46.42 | 25.95 ± 37.46 | 14.27 ± 14.49 |

EXAMPLE 8

The pharmaceutical preparations of dihydroetorphine hydrochloride include a parenteral injectable sterile solution and a sublingual tablet.

(a) Preparation of injectable dihydroetorphine hydrochloride

This injectable is a pharmaceutical preparation in a sterile aqueous solution. Its outward appearance is transparent and colorless. Each ampule contains 20 μg of said compound as the active ingredient in 1 mL of solution.

The prescription is shown as follows:

| Dihydroetorphine hydrochloride | 20 mg |
|---|---|
| 0.001 N Hydrochloric acid | q.s. 1000 mL |

(b) Preparation of dihydroetorphine hydrochloride sublingual tablet

The outward appearance of the sublingual tablet is white. Each tablet contains 20 μg or 40 μg of said compound as active ingredient.

For example, the prescription for 10000 tablets at 40 μg per tablet is as follows:

| Dihydroetorphine hydrochloride | 400 mg |
|---|---|
| Lactose:starch:mannitol:sucrose (3:1:3:3) | 600 g |
| Sodium carboxymethyl cellulose (1% aque sol'n) | 18 mL |
| Ethyl alcohol (50%) | 24 mL |
| Magnesium stearate | 6 g |

According to the above-mentioned prescription, a designated amount of dihydroetorphine hydrochloride was weighed and dissolved in 50% ethyl alcohol. This solution was added dropwise onto excipients under mechanical stirring to ensure uniformity. Meanwhile, 1% sodium carboxymethyl cellulose solution was added dropwise. The soft material thus formed was screened through a 20-mesh sieve and the same operation was repeated for 3 times. The product was then dried in an oven at 60° C. Magnesium stearate was added as a lubricating agent for the tablets.

We claim:

1. A method of treating opioid addiction which comprises administering sublingually, intramuscularly or intravenously an effective amount of a non-addictive opioid analgesic selected from the group consisting of etorphine and dihydroetorphine, to a patient for a first time sufficient for immediate relief or suppression of withdrawal symptoms due to said opioid addiction; administering an effective amount of an replacement opioid for a second time sufficient to maintain said relief or said suppression; followed by administering decreasing amounts of said non-addictive opioid analgesic for a third time sufficient to wean said patient from said analgesic.

2. The method of claim 1 wherein said replacement opioid is methadone.

3. The method of claim 1 wherein said amount of said analgesic is from about 10 µg to about 1000 µg per day.

4. The method of claim 1 wherein said amount of said replacement opioid is from 5 to about 100 mg/day.

5. The method of claim 2 wherein said amount of said analgesic is from about 10 µg to about 1000 µg per day.

6. The method of claim 1 wherein said first time is from about 1 to about 3 days, said second time is from about 1 to about 3 days, said third time is from about 1 to about 8 days and the sum of said first, second and third times is from about 3 to about 14 days.

* * * * *